(12) United States Patent
Strous et al.

(10) Patent No.: US 6,855,546 B1
(45) Date of Patent: Feb. 15, 2005

(54) CONTROLLING AVAILABILITY OR ACTIVITY OF PROTEINS BY USE OF PROTEASE INHIBITORS OR RECEPTOR FRAGMENTS

(75) Inventors: Gerardus Jacobus Antonius Maria Strous, Haaften (NL); Petrus J. M. Van Kerkhof, Beneden Leeuwen (NL); Roland Marinus Theodorus Govers, Utrecht (NL)

(73) Assignee: Universiteit Utrecht, Utrecht (NL)

( * ) Notice: Subject to any disclaimer, the term of this patent is extended or adjusted under 35 U.S.C. 154(b) by 342 days.

(21) Appl. No.: 09/660,302

(22) Filed: Sep. 12, 2000

Related U.S. Application Data

(63) Continuation of application No. PCT/NL99/00136, filed on Mar. 12, 1999.

(51) Int. Cl.$^7$ .............................................. C12N 5/00
(52) U.S. Cl. ................................................ 435/375
(58) Field of Search ............................. 435/375; 514/1, 514/2

(56) References Cited

U.S. PATENT DOCUMENTS 5,756,764 A * 5/1998 Fenteany et al.

FOREIGN PATENT DOCUMENTS

| WO | WO 95/23222 | 8/1995 |
| WO | WO 99/46298 | 9/1999 |

OTHER PUBLICATIONS

Abstract, XP–002112905, 1 page.
Corey et al., "Studies on the Total Synthesis of Lactacystin. An Improved Aldol Coupling Reaction and A β–Lactone Intermediate in Thiol Ester Formation", *Tetrahedron Letters*, vol. 34, No. 44, pp. 6977–6980, 1993.
Govers et al., "Identification of a novel ubiquitin conjugation motif, required for ligand–induced internalization of the growth hormone receptor", *The EMBO Journal*, vol. 18, No. 1, pp. 28–36, 1999.
Govers et al., "Linkage of the ubiquitin–conjugating system and the endocytic pathway in ligand–induced internatlization of the growth hormone receptor", *The EMBO Journal*, vol. 16, No. 16, pp. 4851–4858, 1997.
Hicke, Linda, "Ubiquitin–dependent internalization and down–regulation of plasma membrane proteins", *The FASEB Journal*, vol. 11, pp. 1215–1226, Dec. 1997.
Lee et al., "Selective Inhibitors of the Proteasome–dependent and Vacuolar Pathways of Protein Degradation in *Saccharomyces cerevisiae*", *The Journal of Biological Chemistry*, vol. 271, No. 44, pp. 27280–27284, 1996.
PCT International Preliminary Examination Report, PCT/NL99/00136, dated Jun. 30, 2000.
Strous et al., "Growth Hormone–induced Signal Transduction Depends on an Intact ubiquitin System", *The Journal of Biological Chemistry*, vol. 272, No. 1, pp. 40–43, 1997.
Strous et al., "The ubiquitin conjugation system is required for ligand–induced endocytosis and degradation of the growth hormone receptor", *The EMBO Journal*, vol. 15, No. 15, pp. 3806–3812, 1996.

* cited by examiner

Primary Examiner—Terry McKelvey
(74) Attorney, Agent, or Firm—TraskBritt

(57) ABSTRACT

The invention relates to the field of proteins, more specifically to those proteins that are located on the surface of the cell. The invention, amongst others, provides an inhibitor or pharmaceutical composition that is capable of inhibiting down-regulation of a cell surface receptor. The invention provides a method to control or up-regulate hormone activity by using inhibitors or reagents that modify down-regulation of a protein. The invention further provides a method to control or up-regulate protein activity wherein ligand-induced receptor uptake and/or degradation by endocytosis of a receptor is inhibited, preferably by inhibiting the ubiquitin/proteasome system.

9 Claims, 5 Drawing Sheets

CONTROLLING AVAILABILITY OR ACTIVITY OF PROTEINS BY USE OF PROTEASE INHIBITORS OR RECEPTOR FRAGMENTS

CROSS-REFERENCE TO RELATED APPLICATION

This application is a continuation of PCT/NL99/00136, filed on March 12, 1999, designating the United States of America, corresponding to PCT International Publication WO99/46298 (published in English on Sep. 16, 1999), the contents of which are incorporated herein in its entirety.

TECHNICAL FIELD

The invention relates to the field of regulating metabolic processes, for example, regulating availability and/or activity of proteins such as (cytosolic) transport proteins, enzymes and cytosolic or membrane-bound receptor proteins.

BACKGROUND

A receptor protein on the surface of a cell has a binding site with a high affinity for a particular signaling substance (a hormone, pheromone, neurotransmitter, etc.). The specific signaling substance is often referred to as the ligand, a substance that binds to or fits in a site, the ligand binding site. When the signaling substance binds to a receptor, a receptor-ligand complex initiates a sequence or cascade of reactions that changes the function of the cell. A cell surface receptor polypeptide typically comprises an extracellular part which comprises a binding site where the ligand can interact, a transmembrane part that locates a receptor in the cell membrane, and an intracellular part that plays a role in transducing a signal further into the cell once a ligand has bound. A receptor polypeptide can span the cell membrane several times resulting in multiple extra- and intracellular domains.

The response of a cell or tissue to, for example, specific hormones is dictated by the particular receptors it possesses and by the intra- or intercellular reactions initiated by the binding of any one hormone to its receptor. One cell may have two or more types of receptors or various cell types may have different sets of receptors for the same ligand, each of which induces a different response, or the same receptor may occur on various cell types, and binding of the said ligand may trigger a different response in each type of cells. Clearly, different cells respond in a variety of ways to the same ligand, depending on a receptor or its interaction with the cell.

A wide variety of receptors specific for a wealth of ligands exists. Examples can be found among ion-channels, such as $Ca^+$-channels, or $Cl^-$-channels or $Na^+$-channels, glucose transporters; among immunoglobulin receptors, such as IgE receptors; among cytokine receptors; among multi-drug transporters, and so on. "Receptors," as defined herein, relate to signal-transducing molecules in the broadest sense. These transducing molecules include ion pump-like proteins. For example, the above-mentioned ion channels that transport the ligand (here the ion) through the membrane include receptors that bind to a ligand (eliciting a signal over the membrane) but that do not transport the ligand itself through the membrane, include transport proteins, and include enzymes that act upon contact with a substrate. As an example, receptors having a hormone as a ligand are herein discussed in more detail; however, physiological mechanisms regulating hormone receptor availability and signal transduction are also found among a large variety of receptors having another ligand.

Hormones reacting with cell surface receptors are of a varied nature. Typical examples are amino acid derivatives such as epinephrine or histamine, prostaglandins, various peptide hormones such as glucagon, insulin, gastrin, secretin, ACTH, LH, FSH, TSH, TRH, LHRH, vasopressin, IGF-I or II, EGF, somatotropin (growth hormone), prolactin, erythropoietin, EGF, and others.

These hormones all act by binding to their specific surface receptor, after which their specific signal is being transduced directly or by an intracellular signaling substance (a second messenger), leading to the specific action that is required of the cell.

The amount of functional (hormone) receptor on the cell surface is not constant. A receptor level is modulated up (up-regulation) or down (down-regulation), permitting the cell to respond to small changes in the hormone (ligand) level. The number of cell surface receptors is often down-regulated by endocytosis, whereby the sensitivity of the cell for the specific hormone (ligand) is reduced.

In general, when a ligand (hormone) binds to its receptor and results in a ligand-receptor complex, two phenomena occur. On the one hand, the signal transduction cascade is initiated, while on the other hand, the ligand-receptor complexes are brought in the cell by receptor-mediated endocytosis and the internalized ligand (hormone) is degraded. Internalization and degradation most likely terminate the hormone signal.

Some receptors recycle to the cell surface by exocytosis; however, even if they do, often a substantial fraction will be in the internal membrane compartments at any one time. Fewer receptors will be on the cell surface, available to bind extracellular hormone. Other receptors get degraded by proteolytic cleavage processes in the cell and thus do not, or only insignificantly, recycle to the cell surface, again reducing the number of available receptors on the cell surface.

Another way by which receptor availability on the cell surface is down-regulated is by removal, for example, by specific proteolysis, of the extracellular part that comprises parts of the binding site of a receptor. Such removal is in essence a physiological mechanism that serves to refresh the available receptors and replace them with new ones; however, it again is a factor in reducing receptor availability.

As a consequence of fewer functional receptors being available on the cell surface, the hormone concentration necessary to induce the physiological response is higher and the sensitivity of the cell to the hormone is reduced. The susceptibility of a cell or tissue to the action of a hormone is, thus, among others, dependent on the number of functional receptors present at any given time on the surface of a cell. Even when ligands are circulating at a high concentration, these cannot result in sufficient activation when not enough receptors are present.

Many hormonal-related or other diseases would benefit from an up-regulation of hormone or ligand activity. In hormonal dysfunctioning, one often attempts to achieve such up-regulation simply by treating a patient with exogenous hormones; however, as explained above, such a treatment may not be effective due to the fact that the number of available surface receptors for that hormone are too low. This is often aggravated by the fact that higher hormone concentrations, enhance, by feed-back mechanisms, the further down-regulation of the specific receptor. Exogenous hormone therapy may then even be counterproductive because the patient becomes less susceptible to the hormone in question.

There is thus a need for pharmacological tools or medication that can up- or down-regulate the presence or signal transduction of ligand-specific proteins, such as transport proteins, enzymes, cytosolic receptors or receptors on the surface of cells, for example, to result in a patient responding better to hormonal therapy or to provide the cells of the patient with a higher sensitivity to an endogenous hormone or other ligand.

SUMMARY OF THE INVENTION

The invention provides a method for controlling or up-regulating the availability or activity of a protein comprising regulating or mimicking binding of the ubiquitin/proteasome system at the ubiquitin/proteasome system binding site of the protein, the protein, for example, being a transport protein, an enzyme, a cytosolic receptor protein or cell-surface receptor protein.

The invention also provides a (poly)peptide or (poly)peptide analogue or mimeticum that is derived from, competes with, or binds to, an amino acid sequence located at or around a ubiquitin/proteasome system binding site located in a protein, the protein, for example, being a transport protein, an enzyme, a cytosolic receptor protein, or cell-surface receptor protein. Herewith the invention provides means for applying a method for controlling or up-regulating the availability or activity of a cytosolic receptor protein or transport protein, such as rab7 or rab9 GTPases or Glut4, an enzyme, such as fructose-1, 6-diphosphatase (FBPase) or a cell-surface receptor, such as a growth hormone receptor (GHR).

Through binding at the binding site, the ubiquitin/proteasome system plays a regulating role with a large number of important metabolic processes. Anabolic regulating mechanisms (i.e., acting through GHR, FBPase, Glut4, etc., for example involved in gluconeogenesis) are in this way kept in balance by the catabolic acting ubiquitin/proteasome system. Increased activity of catabolic processes (for example through corticosteroid action) causes down-regulation of anabolic mechanisms.

In a preferred embodiment, the invention provides a (poly)peptide or (poly)peptide analogue or mimeticum according to the invention wherein the binding site comprises the amino acid sequence motif xEFIxxDx (SEQ ID NO:1) or a sequence essentially corresponding thereto.

The invention, for example, provides a method for controlling or up-regulating the availability and/or signal transduction capability of a cell surface receptor comprising providing an inhibitor capable of inhibiting proteolytic cleavage or truncation of the receptor. The proteolytic cleavage or truncation of a receptor provides the basis for down-regulation since cleavage at either the extracellular or intracellular part of a receptor renders the receptor unavailable for ligand interaction and/or signal transduction, thus inhibiting the proteolytic cleavage or truncation of a receptor therefor and provides a longer or more dense receptor availability at the cell surface and better signal transduction to the cell. Also, an increased transport of a transporter/receptor from the intracellular compartments to the cell-surface and/or a decreased transport of a transporter/receptor from the cell surface to intracellular compartments is now induced, whereby the average time that a transporter/receptor stays at the surface of the cell is increased.

The invention provides a method wherein the inhibitor is capable of inhibiting proteolytic cleavage or truncation of an extracellular part of the receptor. An example of such extracellular cleavage is given in the experimental part of this description wherein such truncation or cleavage comprises removal of a 60 kD fragment comprising a soluble growth hormone (GH) binding protein from the extracellular domain of the growth hormone receptor (GHR) from a 70 kD fragment comprising a transmembrane and intercellular part of the receptor. The proteolytic cleavage or truncation preferably occurs at or around the amino acid sequence CEEDFYR (SEQ ID NO:7) found, for example, in the growth hormone receptor.

A preferred embodiment provided by the invention is a method wherein the inhibitor is capable of inhibiting proteolytic cleavage or truncation of an intracellular part of the receptor. An example of such intracellular cleavage is given in the experimental part of this description wherein such truncation or cleavage preferably is initiated by the action of the ubiquitin conjugating system, after which the proteasome can initiate proteolytic cleavage or truncation. We have detected that this ubiquitin/proteasome system is involved in ligand-induced degradation of cell surface receptors. Binding of hormone initiates signal transduction and, at the same time, the ubiquitin/proteasome system is activated and leads to endocytosis and/or degradation of a receptor. Inhibiting the tibiquitin/proteasome system, for example, by preventing ubiquitin and/or the ubiquitin conjugating system to bind to its intracellular binding site at a receptor, prevents this down-regulation from happening and leads to prolonged or more intense signal transduction, thus increasing the ligand activity independent of increased ligand concentration. According to preferred embodiments of the invention, the ligand is a hormone (see examples above), preferably a growth hormone, or the receptor is a hormone receptor (of which various examples are given throughout the description), preferably a growth hormone receptor.

The invention provides means and methods to control or up-regulate exogenous and/or endogenous ligand (for example a hormone) activity by using specific inhibitors or inhibiting reagents, such as peptides or peptide analogues, that control (inhibit, counteract or modify) down-regulation of a cell surface receptor. The invention provides a method or an inhibitor for controlling or up-regulating, for example, cell surface receptors for hormones such as tyroxine, amino acid derivatives such as epinephrine, histamine or glutamine, prostaglandins, peptide or protein hormones such as glucagon, insulin, gastrin, secretin, ACTH, LH, FSH, TSH, TRH, LHRH, vasopressin, IGF-I or II, EGF, somatotropin (growth hormone), prolactin, erythropoietin, leptin, nerve growth factor, EGF, FAS, or that are cytokines. Also, transport proteins, such as calcium-, sodium-, potassium-, chloride-, proton-channel proteins, and glucose transport proteins (for example Glut4) and cytosolic (non-membrane) proteins such as small GTP-binding protein Rab 7 or 9 and fructose-1,6-diphosphatase (FBPase) are receptors or (transport) proteins (examples are CFTR, aquaporins, ENAC, see also Table 1) that can now be controlled or up-regulated by a method provided by the invention.

The invention also provides an inhibitor capable of inhibiting proteolytic cleavage or truncation of a cell surface receptor, for example, for use in a method provided by the invention. One embodiment of the invention is an inhibitor which is capable of inhibiting proteolytic cleavage of the ligand binding site of the extracellular part of the receptor. An example of such an inhibitor provided by the invention is an inhibitor which is capable of inhibiting removal of a 60 kD fragment comprising a soluble growth hormone (GH)

binding protein from the extracellular domain of the growth hormone receptor (GHR) from a 70 kD fragment comprising a transmembrane and an intracellular part of the receptor. The inhibitor can be an inhibitor of proteolytic cleavage per se, being broadly specific for a variety of proteolytic enzymes or being narrowly specific for the distinct proteolytic enzyme or enzymes involved. A preferred embodiment of an inhibitor provided by the invention comprises a (poly)peptide or (poly)peptide analogue that is derived from, competes with, or binds to, an amino acid sequence located at or around a proteolytic cleavage signal site located in the extracellular part of a cell-surface receptor. An example of such a cleavage signal site comprises the amino acid sequence CEEDFYR (SEQ ID NO:7) (or a sequence essentially corresponding thereto) found in the extracellular polypeptide part of a growth hormone receptor.

Another inhibitor according to the invention is an inhibitor which is capable of inhibiting ligand-induced receptor uptake and/or degradation by endocytosis of the receptor, for example, an inhibitor which is capable of inhibiting ligand-induced receptor uptake and/or degradation by the ubiquitin/proteasome system. We have detected that the ubiquitin/proteasome system is involved in ligand-induced degradation of cell surface receptors. Binding of ligand to a receptor initiates signal transduction and, at the same time, the ubiquitin and/or ubiquitin/proteasome system is activated by binding to the intracellular part of the receptor which leads to endocytosis and/or proteolytic cleavage or truncation of a receptor. Inhibiting the ubiquitin/proteasome system prevents this down-regulation from happening and leads to prolonged or more intense signal transduction, thus increasing the hormonal activity independent of increased hormone concentration.

The invention provides an inhibitor capable of inhibiting proteolytic cleavage of the intracellular part of a cell surface receptor. The inhibitor can be an inhibitor of proteolytic cleavage per se, being broadly specific for proteolytic enzymes or being narrowly specific for the distinct protcolytic enzyme or enzymes involved, or can be an inhibitor of ubiquitin binding, whereby further proteolytic cleavage is prevented. A preferred embodiment of an inhibitor provided by the invention is a proteasome inhibitor, for example, selected from the group of proteasome inhibitors, such as MG132, carboxybenzyl-leucyl-leucyl-leucinal, lactacystin, carboxybenzyl-leucyl-leucyl-leucyl vinylsulfone or the β-lacton form of lactacystin.

Another preferred embodiment of an inhibitor provided by the invention comprises a (poly)peptide or (poly)peptide analogue that is derived from, competes with, or binds to, an amino acid sequence located at or around a ubiquitin and/or ubiquitin/proteasome system binding site located in the intracellular polypeptide part of a cell-surface receptor. An example of such a binding site comprises the amino acid sequence motif xEFIxxDx (SEQ ID NO:1), or a sequence essentially corresponding thereto, found in the intracellular polypeptide part of a receptor.

"Essentially corresponding" means herein that the amino acid motif provided by the invention relates to a variety of specific amino acid sequences. For example, the amino acid E (glutamic acid) in the motif can be replaced by the like amino acid D (aspartic acid), F (phenylalanine) can be replaced by Y (tyrosine), I (isoleucine) by L (leucine), V (valine) or F (phenylalanine), S (serine) by T (threonine), or D by E. Examples of amino acid sequences that are essentially corresponding to the amino acid motif xEFIxxDx (SEQ ID NO:1) are listed in Table 1. A further detailed example is the amino acid sequences D-D-S-W-V-E-F-I-E-L-D-I (SEQ ID NO:2) or D-S-W-V-E-F-I-E-L-D (SEQ ID NO:3), located, for example, at a distance of about 50 amino acid residues from the plasma membrane in the intracellular part of the growth hormone receptor. Conversion of each of the 12 amino acids in the motif into alanine residues showed that each amino acid contributes (albeit with varying intensity) to the possible interaction between hormone receptor and ubiquitin or the ubiquitin/proteasome system, and thus to the mechanism of the ubiquitin/proteasome-dependent endocytosis and cleavage of a receptor. Experiments with $^{125}$I-labeled growth hormone demonstrated that, in particular, the conversions of $S^{323}$->A, $E^{326}$->A, $F^{327}$->A, $I^{328}$->A and $D^{331}$->A in the growth hormone receptor affected endocytosis of growth hormone (100% effects), while conversion of the amino acid positions $D^{321}$, $D^{322}$, $W^{324}$ $E^{329}$ $L^{330}$ 1332 into alanine resulted in intermediate effects; mutation $V^{325}$->A did not affect the interaction. Growth hormone receptors with tail truncations of up to amino acid $D^{334}$ functioned as wild-type receptors with respect to the interaction of the presently invented system. Thus, the above-mentioned amino acid motif or variations therein are instrumental for interaction with ubiquitin and/or with the ubiquitin/proteasome system in endocytosis and/or cleavage of a receptor.

The invention provides an inhibitor that is capable of inhibiting down-regulation of the cell surface receptor of a hormone wherein the hormone is selected from a group composed of amino acid derivatives, prostaglandins, peptide or protein hormones and cytokines. Hormones such as tyroxine, amino acid derivatives such as epinephrine, histamine or glutamine, prostaglandins, peptide or protein hormones such as glucagon, insulin, gastrin, secretin, ACTH, LH, FSH, TSH, TRH, LHRH, vasopressin, IGF-I or II, EGF, somatotropin (growth hormone), prolactin, erythropoietin, leptin, nerve growth factor, EGF, FAS, or that are cytokines. Also, transport proteins, such as glucose transporter, calcium-, sodium-, potassium-, chloride- and proton-channel proteins, are receptors (examples are CFTR, aquaporins, ENAC) that can now be controlled or up-regulated by an inhibitor provided by the invention. The invention provides a (poly)peptide or (poly)peptide analogue or mimeticum derived from an amino acid sequence that corresponds to the amino acid motif CEEDFYR (SEQ ID NO:7), or xEFIxxDx (SEQ ID NO:1) or to a motif essentially corresponding thereto. A (poly)peptide that competes, binds, or interacts in another way with such an amino acid sequence is herein also considered to be derived from an amino acid sequence corresponding to such a motif Such a peptide is selected according to methods known by a person skilled in the art. It is to be expected that the conformation of a selected (poly)peptide is important for its reactivity. Appropriate conformational changes can be introduced in selected (poly)peptides by techniques known to the person skilled in the art. For example, it is possible to introduce appropriate conformation by using di-sulfide bridges. Also, other peptide sequences or compounds, mimicking the wanted conformation (mimetica) can be selected by a person skilled in the art. A suitable system to select a (poly)peptide is a system such as the PEPSCAN system, whereby interaction, such as competition or inhibition, is measured against sets of overlapping peptides chosen from the receptor's amino acid sequence. Analogous peptides, whereby specific amino acids are replaced by others, being either L- or D-amino acids, are similarly tested. Other methods include replacement net scanning of selected peptide sequences, for example, by replacing distinct amino acids by alanine, whereby crucial amino acids in the selected peptides are determined. (Poly)peptides can be made synthetically or via recombinant techniques. Suitable (poly) peptides for up-regulation of GH activity are derived, for example, from the amino acid sequence SKQQRIKMLILPPVPVPKIKGIDPDLLKEGKLEEVNTI-LAIHDSYKPEFHSDDSWVEFIELD IDEPDEKTEES-DTDRLLSSDHEKSHSNLGVKDGDSGRTSCCEPDIL-ETDFNANDIHEGTSE VAQPQRL (SEQ ID NO:4) found with the growth hormone receptor. An example of such a selected sequence comprises the amino acid sequence SWVEFIELDIDD (SEQ ID NO:51) or variations thereon as, for example, shown in Table 1. Another example is the sequence KDGDSGRTSCCEPDILETDFNANDI-HEGTSEVAQPQRL (SEQ ID NO:5) that comprises a signal site allowing the proteasome to stop, after which endocytosis occurs.

Furthermore, the invention provides a pharmaceutical composition comprising an inhibitor that is capable of controlling the availability and/or signal transduction capability of a cell surface receptor or inhibiting down-regulation of a cell surface receptor according to the invention, for example, by regulating the activity of a hormone. Such a pharmaceutical composition, for example, finds its use in treating patients with hormone deficiencies, such as growth hormone deficiencies. Yet another example of use of a pharmaceutical composition provided by the invention is for the treatment of patients that are suffering from (muscle) wasting that results from increased (muscle) protein degradation that is often seen after or during disorders such as renal tubular defects, uraemia, diabetes, Cushing's syndrome, cachexias seen with cancer or with eating disorders, after serious burns, during sepsis or AIDS, after stress, during and after immobilization, during neuromuscular disease, and other conditions that alter protein degradation in cells such as muscle cells. Experimental animal models are available to study these and other related disorders. One can, for instance, use rats to study fasting, metabolic acidosis, kidney failure, muscle denervation, diabetes, thermal injury, endotoxaemia, bacteraemia, tumor development, glucocorticoid or thyroid hormone treatment and hyperthyroidism. Studies of such experimental models have indicated that the ubiquitin/proteasome pathway is activated in muscle and causes the loss of muscle mass (wasting) in these disorders. The invention provides the use of pharmaceutical compositions inhibiting this pathway and controlling or up-regulating the availability of hormone receptors, such as growth hormone receptors, thereby activating anabolic processes in the cells and decreasing the protein degradation seen with the above-described disorders related to muscle wasting.

Yet another embodiment of the invention is a pharmaceutical composition comprising an inhibitor provided by the invention, which composition is administered in conjunction with a hormone. The term "in conjunction," as used herein, means the composition is used or applied before, during or after hormonal treatment and up-regulates or modifies the activity of the hormone.

Yet another embodiment of a method provided by the invention is a method wherein up-regulation of hormone receptors is achieved via preventing ligand-induced receptor-mediated uptake and degradation by endocytosis mediated via the intracellular part of a receptor. A preferred embodiment of the invention is a method whereby the ubiquitin/proteasome system that is involved in ligand-induced degradation of a hormone receptor is inhibited. We have detected that ubiquitin conjugation and/or subsequent proteasome action (the ubiquitin/proteasome system) is involved in ligand-induced degradation of cell surface receptors. Binding of hormone initiates signal transduction and at the same time the ubiquitin/proteasome system is activated and leads to endocytosis and/or degradation of a receptor. Inhibiting the ubiquitin/proteasome system prevents this down-regulation from happening and leads to longer or higher signal transduction, thus increasing the hormonal activity independent of increased hormone concentration.

Also, the invention provides a method for controlling or up-regulating the availability of the Glut4 insulin-regulated glucose transporter (Glut4). Herein, interaction with the ubiquitin/proteasome system is regulated through binding at an amino acid motif TELEYLGPDE (SEQ ID NO:6) (see Table 1). Regulating the interaction allows for regulating endocytosis of Glut4. By down-regulating endocytosis of Glut4 with a method according to the invention, the invention provides a novel way of treating diabetes, type I as well as type II. High glucose plasma levels can now be reduced or tampered independent from regulating insulin or insulin-receptor levels.

The invention provides a method for controlling or up-regulating the availability of a large variety of cell surface receptors. It has now been found that the turnover of these receptors can be regulated by ubiquitin binding, for example, in the ubiquitin/proteasome system. Inhibiting the system prevents or retards turn-over of the receptors and may lead to longer or higher signal transduction, thus increasing the hormonal activity independent of increased hormone concentration. The invention provides a method or an inhibitor for controlling or up-regulating, for example, cell surface receptors for hormones such as tyroxine, amino acid derivatives such as epinephrine, histamine or glutamine, prostaglandins, peptide or protein hormones such as glucagon, insulin, gastrin, secretin, ACTH, LH, FSH, TSH, TRH, LHRH, vasopressin, IGF-1 or 11, EGF, somatotropin (growth hormone), prolactin, erythropoietin, leptin, nerve growth factor, EGF, FAS, or that are cytokines. Also, transport proteins, such as calcium-, sodium-, potassium-, chloride- and proton-channel proteins are receptors (examples are glucose transporters, CFTR, aquaporins, ENAC, see also Table I) that can now be controlled or up-regulated by a method provided by the invention. The invention provides means and methods to control the action of the ubiquitin/proteasome system to up-regulate hormone activity by using specific inhibitors of proteasome action or by using reagents that compete for the ubiquitin/proteasome system recognition sites on a receptor or membrane channel.

An example of a method provided by the invention is given in the experimental part, where a method inhibiting the ubiquitin/proteasome system that is involved in ligand-induced degradation of a growth hormone receptor is further explained. The growth hormone receptor is important for normal growth and development in animals and humans. Biological effects include linear growth, lactation, nitrogen retention, lipolysis, diabetogenic-like effects, macrophage activation, and others. Binding of growth hormone induces dimerization of two receptor polypeptides. This double binding initiates signal transduction and at the same time the ubiquitin/proteasome system is activated and removes a considerable part of the cytosolic or intracellular tails of a receptor. This proteolytic event is an obligatory step in the cascade of reactions which lead to endocytosis and degradation of a receptor. The invention provides means and methods to control the action of the ubiquitin/proteasome system to up-regulate growth hormone activity by using inhibitors such as specific inhibitors of proteasome action or reagents that compete for the ubiquitin/proteasome system recognition sites on a receptor.

The invention also provides the use of a proteasome inhibitor, for example, MG132, carboxybenzyl-leucyl-leucyl-leucinal, lactacystin, carboxybenzyl-leucyl-leucyl-leucyl vinylsulfone or the β-lacton form of lactacystin, for the production of a pharmaceutical composition. As an example, the invention provides the use of such a proteasome inhibitor for the production of a pharmaceutical composition regulating the activity of a hormone, such as a growth hormone. Furthermore, the invention provides the use of such a proteasome inhibitor for the production of a pharmaceutical composition regulating the activity of a hormone wherein the composition is administered in conjunction with the administration of the hormone.

The invention also provides the use of a peptide or peptide analogue competing with and derived from an intracellular or extracellular protein part of a receptor respectively. For example, a peptide or peptide analogue comprising the amino acid motif CEEDFYR (SEQ ID NO:7) or xEFIxxDx (SEQ ID NO:1) for the production of a pharmaceutical composition, for example, for controlling the availability and/or signal transduction capability of a cell surface receptor or for regulating the activity of a hormone, such as a growth hormone, wherein the composition may or may not be administered in conjunction with the administration of the hormone.

DETAILED DESCRIPTION

Experimental Part

Degradation of cytosolic proteins is mainly carried out by the 26S proteasome. The ubiquitin conjugation system selects and targets the proteins for proteasomal degradation by proteolytic cleavage (1). Previously, we have shown that the ubiquitin conjugation system is involved in ligand-induced endocytosis of the growth hormone receptor (GHR) (2). Here, we present direct evidence that proteasome action is required for growth hormone (GH) to be internalized by its receptor. In the presence of specific proteasome inhibitors, GH internalization was inhibited, while the transferrin receptor cycle was unaffected. Consequently, the half-life of the GHR in the presence of ligand was prolonged by proteasome inhibitors. GH uptake by a truncated GHR proceeded normally in the presence of inhibitors. Experiments with CHO cells harboring a temperature-sensitive ubiquitin-activating enzyme (E1) showed that the ubiquitin conjugating system is required before the proteasome can act upon the GHR.

Figure 1:
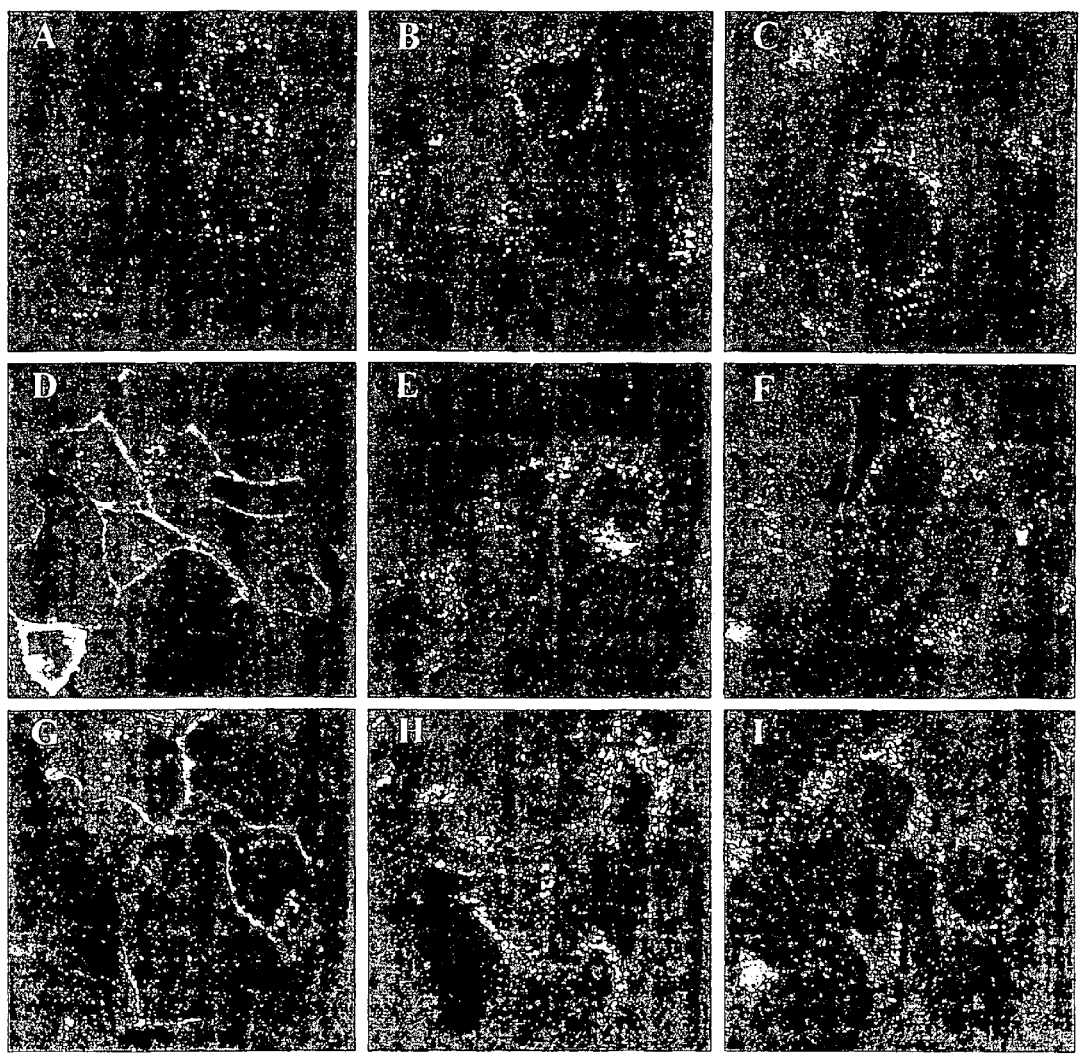
FIG. 1. Effect of proteasome inhibitors on Cy3-GH and Cy3-transferrin endocytosis. CHO-ts20 cells, expressing either wild-type (A, D, G, C, F, I) or truncated GHR (B, E, H), were incubated with vehicle (A–C) or with 20 mM MG132 (D–F) or 20 mM lactacystin (G–I) for 3 hours at 30° C.; then Cy3-GH (A, B, D, E, G, H), or Cy3-transferrin (C, F, I) were added for 30 minutes, and the cells were washed, fixed and the fluorescence was visualized by confocal microscopy. If excess labeled ligand was added, no uptake was observed. If the cells in D, G were treated at pH 2.5 before fixation, virtually no label was visible (not shown).

Down-regulation of signal-transducing membrane receptors is part of highly programmed cascades of events leading both to extinction of the signaling pathway(s) and to rapid degradation of the primary messenger: the receptor and its ligand (3, 4, 5, 6, 7). In the absence of ligand, the half-life of GHR is approximately 1 to 2 hours depending on the cell system used. The assumption is that this is mainly due to a proteolytic cleavage in the extracellular domain of the GHR resulting in soluble GH-binding protein (8). If ligand is present, a completely different scenario follows: two GHR polypeptides dimerize, they are phosphorylated by the tyrosine kinase Jak2 and ubiquitinated, and the complex is endocytosed. As the ubiquitin conjugation system acts generally in concert with the 26S proteasome, we examined the effect of proteasome inhibitors on Cy3-labeled GH uptake. CHO cells carrying a temperature-sensitive E1 enzyme and expressing the rabbit GHR were incubated at the permissive temperature with Cy3-GH (9, 10). Incubation for 30 minutes resulted in abundant fluorescent label in endosomal and lysosomal compartments (FIG. 1A). If the cells were treated with the specific proteasome inhibitors MG132 (FIG. 1D) and lactacystin (FIG. 1G) hardly any label was present intracellularly. The same results were obtained if the cells were treated with carboxybenzyl-leucyl-leucyl-leucyl vinylsulfone or a more membrane-permeable analogue of lactacystin, its b-lactone form (not shown) (11, 12). To ascertain that these proteasome inhibitors did not cause pleiotropic effects on the receptor-mediated endocytotic machinery, we used Cy3-labeled transferrin under identical conditions (FIGS. 1C, 1F, 1I); no inhibition of transferrin uptake was observed. To address the question whether the proteasome acts directly on the GHR, we used CHO cells expressing a GHR, truncated after amino acid residue 369 (GHR 1–369, with amino acid residues 370–620 deleted). FIGS. 1B, 1E, 1H show that the same inhibitors as used for the full-length GHR had no effect on GH endocytosis by the truncated GHR. Most likely, removal of a portion of the cytosolic tail is sufficient to enable endocytosis of GH.

Figure 2:
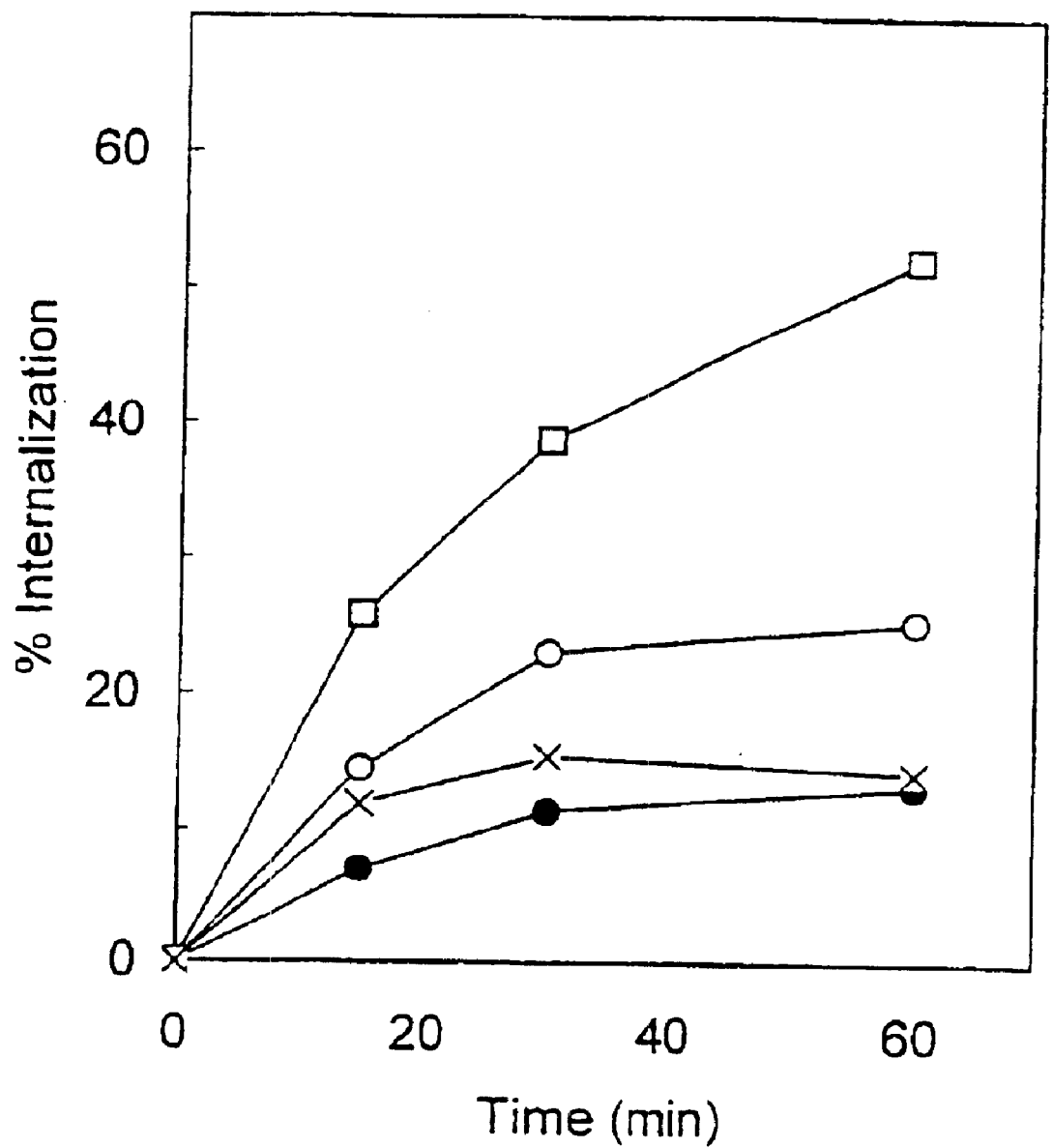
FIG. 2. Proteasome inhibitors inhibit uptake of $^{125}$I-GH. CHO-ts20 cells were incubated with or without inhibitors for 3 hours at 30° C., and put on ice for 60 minutes with $^{125}$I-GH. The cells were then incubated at 30° C. as indicated. Background label was determined in untransfected cells and subtracted. Plotted are the amounts of $^{125}$I-GH internalized as a percentage of the cell-associated radioactivity at the start of incubation. □, control (1% ethanol); ●, MG132; ○, lactocystin; X, lactacystin β-lactone.

To confirm and quantify the effect of the proteasome inhibitors, we measured the uptake of $^{125}$I-GH in a kinetic experiment. Cells were pretreated with the inhibitors, $^{125}$I-GH was bound on ice, and cells were incubated for various periods of time (FIG. 2). At the end of the incubation period, uptake was determined by washing the cells at low pH to remove the label from the cell surface. Again, GH uptake was inhibited by the proteasome inhibitors: MG132 and lactacystin b-lactone reduced the uptake to approximately 25% of the control level. Lactacystin was somewhat less effective, probably due to its poor cell-permeant properties. TCA-soluble radioactivity in the culture medium, derived from lysosomal degradation of $^{125}$I-GH, increased after 15 minutes if no inhibitor was added; virtually no TCA-soluble radioactivity appeared if the inhibitors were present (not shown). These results show that receptor-mediated uptake and degradation of GH is severely inhibited in the presence of proteasome inhibitors.

Figure 3:
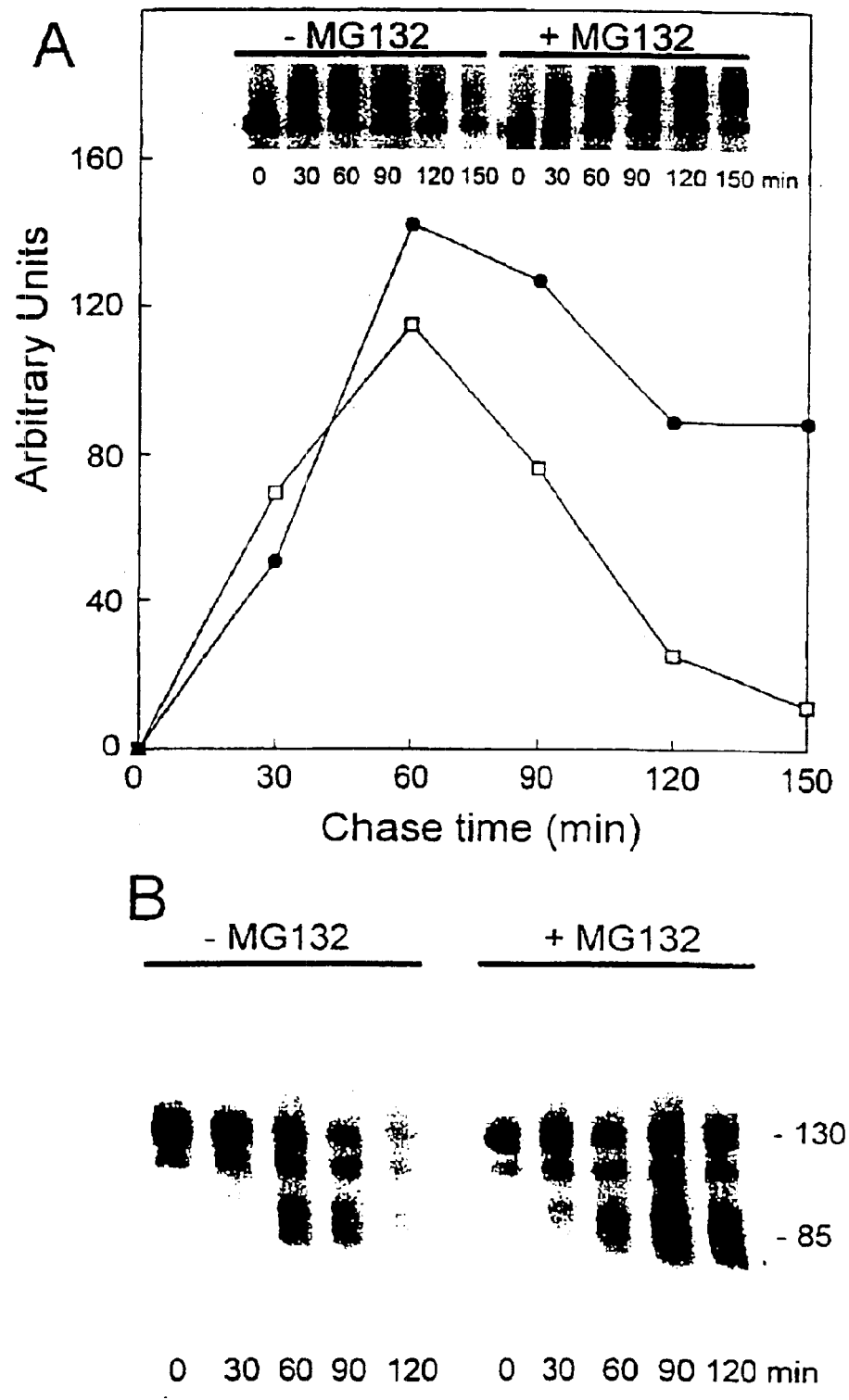
FIG. 3. Effect of MG132 on GHR degradation in the presence of ligand. A. Cells were pulse labeled with $^{35}$S-methionine and then chased in unlabeled methionine in the presence of 16 nM GH with or without MG132 for the times indicated. GHR was immunoprecipitated using an anti-cytosolic tail antibody. The radioactivity in the mature (upper) band (inset) was quantitated and plotted. □, control (1% ethanol); ●, MG132. B. Cells were biotinylated and incubated in the presence of GH with MG132 or with vehicle only at 30° C. for the time periods indicated. After streptavidin-bead purification aliquots of the cell lysates were analyzed by SDS-PAGF; western blots were incubated with a monoclonal antibody specific for the extracellular GHR domain and detected with enhanced chemifluorescence. The sharp band below the mature GHR (130 kDa) originated from a slight background staining of precursor GHR (110 kDa), due to incomplete removal of biotinylation reagent at cell lysis.

If proteasome inhibitors affect GHR-uptake, it is expected that the inhibitors prolong the lifetime of GHRs at the cell surface. To address this, we measured the effect of MG132 in a pulse-chase experiment. FIG. 3A clearly shows that MG132 affects the degradation rate of mature GHR; it does not affect membrane transport from ER to the Golgi complex as is clear from the undisturbed maturation kinetics (i.e., the conversion of 110 kDa species to the mature 130 kDa protein). To assess the effect of MG132 more directly, we measured degradation of cell-surface biotinylated GHR after incubation in the presence of ligand (FIG. 3B). As expected, GH induced a rapid disappearance of the GHR. However, clearance from the cell surface was reduced >50% in the presence of MG132. Interestingly, a biotinylated 85-kDa intermediate degradation product visualized with a monoclonal antibody specific for the extracellular domain appeared transiently. The lifetime of this species was extended in the presence of MG132. Attempts to accumulate this species or other degradation products failed until now. In the absence of GH, biotinylated GHRs had a half-life of approximately 60 to 90 minutes at 30° C., independent of the presence of MG132 as has been shown previously for the steady-state situation (4, 5, 6). Constitutive cleavage of cell surface GHR resulted in soluble GH-binding protein in the culture medium (not shown).

Figure 4:
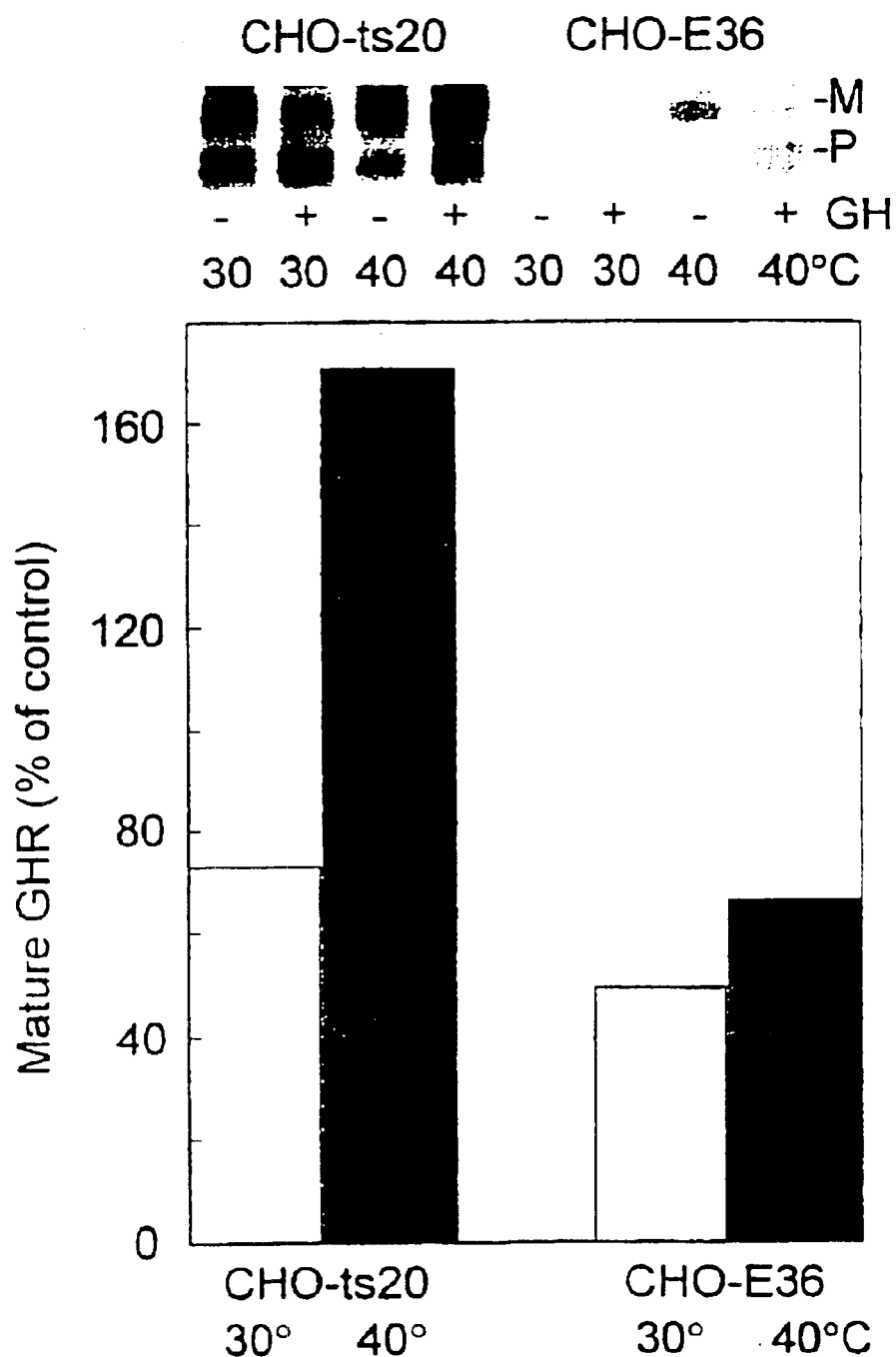
FIG. 4. GH-induced receptor degradation depends on an intact ubiquitin conjugation system. CHO-ts20 and CHO-E36 cells were incubated at the permissive or non-permissive temperature for 3 hours in the presence or absence of GH. Cells were lysed and aliquots were analyzed by western blotting and enhanced chemifluorescence. M, mature GHR, P, precursor GHR. The lower panel shows the quantification (expressed as percentage of mature GHR present without GH).

To investigate whether the ubiquitin system selects the GHR for truncation by the proteasome, we expressed the receptor in CHO-ts20 cells harboring a temperature-sensitive ubiquitin-activating enzyme, E1. The cells were incubated for 60 minutes at 42° C. (sufficient to stop generation of newly ubiquitinated proteins), followed by 3 hours at 40° C. in the presence or absence of GH, and the amounts of GHR were determined by quantitative western blot analysis (FIG. 4). At the permissive temperature, incubation in the presence of GH decreased the steady-state amounts of GHR. If the cells were kept at 40° C. in the presence of GH, the amount of GHR increased to 170%. To ascertain that this increase is solely due to a defective ubiquitin conjugation system, we used the CHO-E36 cells with an intact ubiquitin conjugation system at 40° C. As expected, in these cells the steady state of mature GHR decreased to approximately 50% of that without GH, both at 30 and 40° C. The experiment clearly shows that if the ubiquitin system is switched off, the GHR is stabilized in the presence of GH, rather than degraded as is the case in the (wild-type) CHO-E36 cells. The conclusion is that the ubiquitin conjugation system targets the GHR for partial degradation by the proteasome.

It has been generally accepted that the ubiquitin/proteasome system is involved in selective degradation of cytosolic and nuclear proteins (1). At the cytosolic face of the endoplasmic reticulum, the ubiquitin/proteasome system is involved in degradation of mal-folded ER proteins (13, 14). In a growing number of cases, the ubiquitin conjugation system seems to be involved in the selecting steps directly preceding endocytosis at the plasma membrane. In yeast, the α-factor receptor Ste2p (15), the Ste6 ABC transporter (16), Gap1p amino acid permease (17), Fur4 uracyl permease (18), and PdrS (19), a multi-drug transporter, are all ubiquitin-dependently endocytosed. Previously, we have shown that GHR endocytosis requires an intact ubiquitin system and that GH internalization is accompanied by GHR ubiquitination (2, 10). Here, we present direct evidence that, for the same event, proteasome action is required as well. The proteasome cleaves or truncates the tail of the dimerized receptor, as truncation of the GHR at amino acid residue 369 renders the ligand-induced endocytosis of the receptor insensitive to the action of proteasome inhibitors. In addition, the transient appearance of an 85-kDa degradation intermediate again demonstrates a proteasome action on the GHR. Previously, we have shown for truncated GHRs that endocytosis and ubiquitination are closely linked events (2, 10). Together, the data support a model in which specific members of the E2/E3 enzyme families recognize and ubiquitinate the dimerized cytosolic GHR tails; this event induces recruitment of 26S proteasomes, which truncate the tail. Only then the receptor-ligand complex can access the coated pits for further transport to the lysosomes. This model also predicts an early abrogation of part of the signal transduction by the proteasome, while the receptor is still at the cell surface.

Furthermore, we present evidence that the proteasome is also involved in growth hormone receptor down-regulation: in the presence of specific proteasomal inhibitors, GH internalization was inhibited, whereas the transferrin receptor cycle remained unaffected. A truncated GH receptor entered the cells independent of proteasome action. Full-length GH receptor disappeared immediately upon endocytosis of ligand. Distal GH receptor tail epitopes became extinct rapidly upon endocytosis; loss of the cytosolic tail was ligand-dependent and preceded degradation of luminal epitopes. Apparently, the proteasome truncates a portion of the growth hormone receptor tail before endocytosis can proceed. This implies that signal transduction continues intracellularly with different characteristics compared to GHR signaling at the cell surface.

Although these findings apply to the GHR function, there are indications that the ubiquitin system is involved in regulating the resident time at the cell surface of other membrane proteins. The Met tyrosine kinase receptor degradation is partly dependent on proteasome action (20), the resident time of the sodium channel protein ENac is regulated by the ubiquitin system (21), while many signaling membrane receptors, e.g., the TCR z-chain (22), the Kit (23), EGF (24), IgE (25, 26), and prolactin (26) receptors, are all ubiquitinated upon activation.

Figure 5:
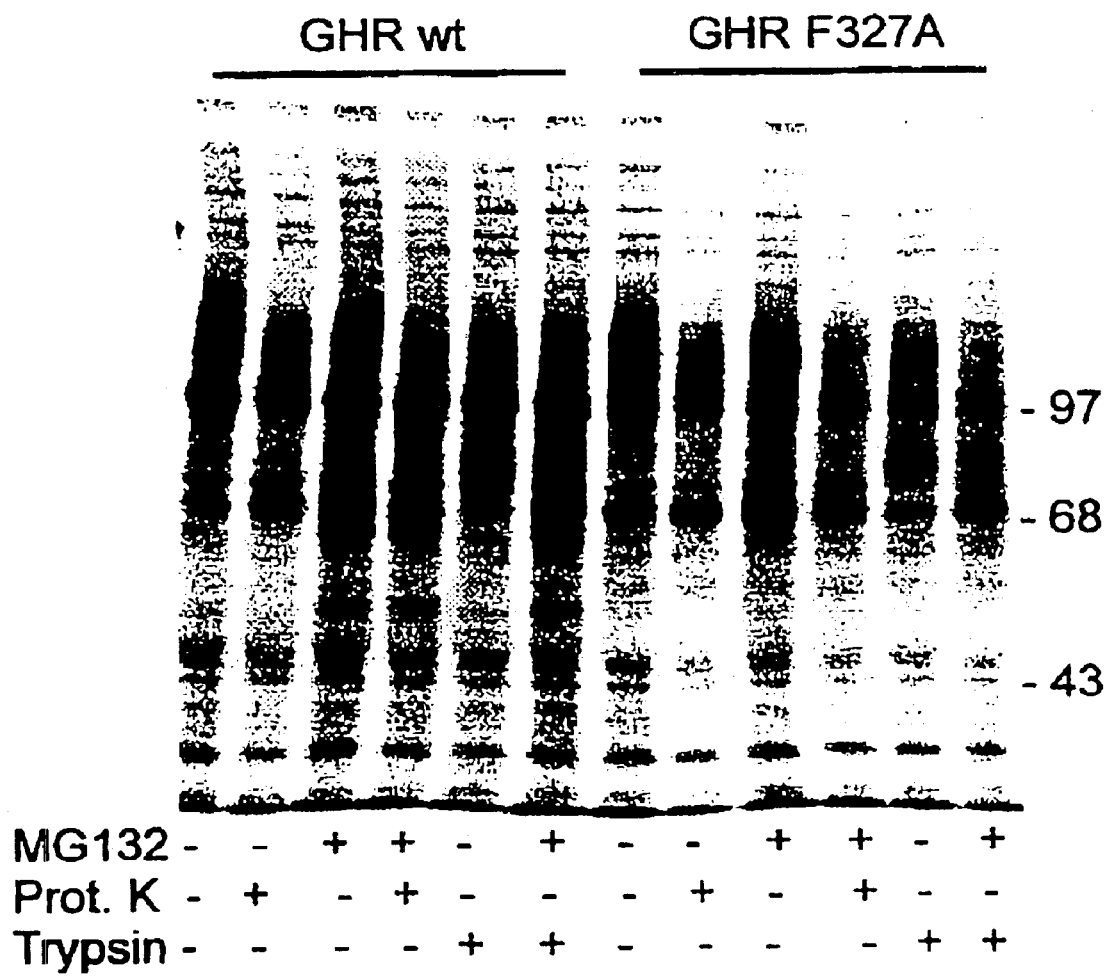
FIG. 5. Proteolytic removal of growth hormone binding protein. Cells (CHO cells expressing GHR-wt or GHR F327A) were labeled in the presence of [$^{35}$S]methionine for 4 hours in the presence or absence of the proteasome inhibitor MG132 (20 μM)$^{10}$. The cells were either treated with proteinase K (0.5 mg/ml) or with trypsin (0.5 mg/ml) on ice for 30 minutes or not treated. The proteases were removed, the cells were lysed, and the radioactively labeled GHR was immunoprecipitated using an anti-cytosolic tail antibody, analyzed by SDS-PAGE, and visualized by phosphoimaging.

Removal of the extracellular portion of the GHR (the binding domain) occurs continuously (at steady state) if a receptor resides at the cell surface and if no ligand (GH) is bound. Comparison of the molecular sizes of the remnant receptor remaining after proteolytic digestion of cells bearing GHR at their cell surface using an aspecific protease like proteinase K, with the size of the remnant receptor cleaved in vivo by membrane-associated endogenous proteolytic activity, demonstrates that the natural cleavage site is very close to the plasma membrane. This is confirmed by the observation that the apparent molecular size of the remnant GHR cleaved with trypsin (cleaving, e.g., after lysine residue 221, 25 amino acids upstream) is approximately 3 kDa larger than observed for that of the in vivo-generated remnant GHR (FIG. 5). The experiment shows that upon proteinase K treatment, the 130 kDa GHR was converted to a 70 kDa species. A similar band was visible if the cells were incubated in the presence of the proteasome inhibitor MG132. If trypsin was used instead of proteinase K, a slightly bigger species was observed. If the phenylalanine-327 was converted to an alanine in the receptor tail (which aborts ubiquitination and endocytosis of the receptor), similar results as occur with wild-type receptors were observed. The conclusion is that the GHR is cut very close to its transmembrane segment by a yet unknown proteolytic enzyme. Combining this finding with the nature of the amino acid sequence 3 kDa downstream from the trypsin-sensitive site, we propose that the specificity of the proteolytic cleavage resides at or around the amino acid sequence CEEDFYR (SEQ ID NO:7).

Methods

Cells and antibodies. A polyclonal antibody to GHR was raised in rabbits against amino acid residues 327–493 as described (10); antibody (Mab5) recognizing the luminal part of the GHR was from AGEN Inc., Parsippany, N.J. A Chinese hamster ovary (CHO) cell line, harboring a temperature-sensitive defect in the ubiquitin activation enzyme E1 (CHO-ts20), was transfected with both the full-length rabbit GHR cDNA sequence and a truncated GHR (1–369) (9, 10). Ten mM sodium butyrate was added to the cells 18 hours before use to increase GHR expression (2, 27). As control, CHO-E36 cells were used stably transfected with GHR.

GH binding and internalization. $^{125}$I-hGH was prepared using chloramine T (28). For internalization studies, cells were grown in 35 mm dishes, washed with aMEM, supplemented with 20 mM HEPES, incubated for 1 hour at 30° C. in aMEM/HEPES, $^{125}$I-GH (8 nM) was bound on ice for 60 minutes in the absence or presence of excess unlabeled GH, and the cells were washed free of unbound GH and incubated for 0 to 60 minutes. If indicated, lactacystin or its b-lactone (20 mM), MG132 (20 mM), and ZL$_3$vinylsulfone (20 mM), dissolved in either ethanol or dimethylsulfoxide, or only vehicle, were added 3 hours before the start of the experiment. Membrane-associated GH was removed by acid wash (0.15 M NaCl, 0.05 M glycine, pH 2.5) (29) and internalized GH was determined by measuring the radioactivity after solubilization of the acid-treated cells by 1 M NaOH.

Cell surface biotinylation. CHO-ts20 cells, grown in 35 mm dishes, were incubated for 60 minutes at 30° C. in aMEN/HEPES, biotinylated on ice for 30 minutes using sulfo-NHS-SS-biotin (Pierce, Rockford, Ill.), and washed free of biotinylating reagents. For GH binding, the cells were incubated for 1 hour on ice in the presence of 16 nM GH with either 20 mM MG132 or 1% ethanol. The incubation was continued at 30° C. for various time periods in the presence of GH with MG132 or ethanol only. Cells were then lysed on ice, and equal aliquots of the cell extracts were incubated with streptavidin beads for 1 hour at 4° C., and washed with PBS.

Metabolic labeling. The cells were incubated in methionine-free MEM for 30 minutes and then $^{35}$S-methionine (TRAN-$^{35}$S label, 3.7 MBq/ml, 40 TBq/mmol, ICN, CA, USA) was added and the incubation was continued for 30 minutes; the radioactivity was chased in the presence of 0.1 mM of unlabeled methionine. Cell lysates were subjected to immunoprecipitation. The radioactivity was determined using a Molecular Dynamics phosphoimager (STORM860 equipped with ImageQuant software, Molecular Dynamics, Sunnyvale, Calif.).

Cell lysis, immunoprecipitation and western blotting. At the end of the incubation, cells were immediately washed and lysed on ice in 0.3 ml of 1% Triton X-100, 1 mM EDTA, 10 mg/ml aprotinin, 10 mg/ml leupeptin, 2 mM MG132, and 1 mM phenylmethylsulphonyl fluoride in PBS. Equal aliquots of the cell extracts were subjected to SDS polyacrylamide gel electrophoresis and immunoblotting as described (2). For detection, we used the enhanced chemifluorescence system (Amersham Corp., UK).

Microscopy. Cy3-GH and Cy3-transferrin were prepared using a Fluorolink-Cy3 label kit according to the supplier's instructions (Amersham, UK). The cells, grown on coverslips, were incubated for 60 minutes in aMEM, supplemented with 20 mM HEPES at 30° C. and for 30 minutes with Cy3-GH (1 mg/ml) or Cy3-transferrin (20 mg/ml). Cells were washed with PBS to remove unbound label and fixed for two hours in 3% paraformaldehyde in PBS. After fixation, the cells were embedded in Mowiol and confocal laser scanning microscopy was performed using a Leica TCS 4D system.

Table 1, Abstract and Sequence Listing attached hereto as Appendix A. A marked-up substitute specification to clearly identify amendments to the specification as required by 37 C.F.R. §§ 1.121(b)(3)(iii) is attached hereto as Appendix B. The application has been amended by adding paragraph numbering in an effort to conform more closely to U.S. practice and to correction grammatical and spelling errors. It is respectfully submitted that the substitute specification does not introduce new matter into the above-referenced patent application.

TABLE 1

| Sequence | Description |
| --- | --- |
| SWVEFIELDI (SEQ ID NO:8) | GHR sequence (human, rabbit . . . ) |
| LWVEFIELDI (SEQ ID NO:9) | GHR chicken |
| LLVEYLEVDD (SEQ ID NO:10) | prolactin receptor, human |
| LLVEFLENDD (SEQ ID NO:11) | prolactin receptor, rabbit, rat, mouse |
| DNVDYLTRDW (SEQ ID NO:12) | $Ca^{++}$-channel vertebrate skeletal muscle |
| QAAEYLRSET (SEQ ID NO:13) | TKR CEK$_2$, PIG (FGF-receptor family) |
| IDAEYISAER (SEQ ID NO:14) | Transmembrane receptor sex precursor |
| LKGEFIWVDG (SEQ ID NO:15) | IgE receptor |
| YGSEYINLDG (SEQ ID NO:16) | angiotensin converting enzyme |
| SEGEYIPLDQ (SEQ ID NO:17) | potassium channel IRK$_1$ |
| DGHEYIYVDP (SEQ ID NO:18) | PDGF receptor α-chain |
| DGHEYIYVDP (SEQ ID NO:19) | PDGF receptor β-chain |
| DNFEYLTRDS (SEQ ID NO:20) | $Ca^{++}$-channel α1β (human, rat, rabbit) |
| KIFEYLRRDT (SEQ ID NO:21) | Cl$^-$-channel, CLC7 |
| SLQEYLQNDT (SEQ ID NO:22) | Tyrosine-protein kinase FRK (human) |

TABLE 1-continued

| | |
|---|---|
| TELEYLGPDE (SEQ ID NO:23) | Glut4 Ins-regulated glucose transporter |
| NQEEYLRYDS (SEQ ID NO:24) | MHC-IIβ (rat) |
| ENPEYLGLDV (SEQ ID NO:25) | ERB2 TKR (neu-oncogene) |
| RLKEYLAGDV (SEQ ID NO:26) | Anion transporter I |
| LYKDFLTLEH (SEQ ID NO:27) | Vascular endothelial growth factor receptor 2 |
| EQLEYLSYDA (SEQ ID NO:28) | Vascular endothelial growth factor receptor 3 |
| PEGEFLPLDQ (SEQ ID NO:29) | G protein-act. inward rectifier K⁺-channel-1 |
| SDSEFLLPDT (SEQ ID NO:30) | Protein-tyrosine phosphatase zeta (human) |
| SALDFIRRES (SEQ ID NO:31) | Glutamate (NMDA) receptor subunit epsilon 2 |
| AHNEYLVSEI (SEQ ID NO:32) | Rhesus blood group-associated glycoprotein |
| VTLDFLDAEL (SEQ ID NO:33) | Dihydropyridine-sensitive 1-type, Ca⁺⁺-channel |
| EISDFLRYEL (SEQ ID NO:34) | Thrombopoietin receptor |
| SAKDYIYQDS (SEQ ID NO:35) | Serotonin receptor 1B (brain) |
| YQQDFFPKEA (SEQ ID NO:36) | Epidermal growth factor receptor |
| SKLQYILAQI (SEQ ID NO:37) | Sodium-, chloride-dependent transporter NTT4 |
| TPLNYILLNL (SEQ ID NO:38) | Rhodopsin |
| TSVDLLDINV (SEQ ID NO:39) | Interleukin-2 receptor β-chain |
| GTPDYIAPEI} (SEQ ID NO:40) | cAMP-dependent protein kinase C, alpha, beta, |
| GTPEYLAPEI} (SEQ ID NO:41) | delta, epsilon, gamma |
| LVFEYLDKDL (SEQ ID NO:42) | Serine-threonine kinase PCTAIRE 1, 2 |
| LVFEYLDSDL (SEQ ID NO:43) | Serine/threonine kinase PCTAIRE 3 |
| IGADFLTKEV (SEQ ID NO:44) | Small GTP-binding protein Rab-7 |
| IGVEFLNKDL (SEQ ID NO:45) | Small GTP-binding protein Rab-9 |
| ISVEFLVLDS (SEQ ID NO:46) | Synaptotagmin IV |
| SDIDFLIEEI (SEQ ID NO:47) | Glutamate decarboxylase (GAD67) |
| AIGEFILVDK (SEQ ID NO:48) | Fructose 1, 6 diphosphatase (FBPase) |
| QKQEYKTLEY (SEQ ID NO:49) | Cystic fibrosis transmembrane conductance regulator (CFTR) |
| PPPxY- (SEQ ID NO:50) >WWdomain of NEDD4 | Epithelial Na⁺-channel (ENaC) |

What is claimed is:

1. A method for reducing binding of a ubiquitin-proteasome system to a cell surface receptor, the method comprising:
contacting a cell with a peptide that specifically inhibits the interaction of an ubiquitin-proteasome segment with an ubiquitin-proteasome binding site comprising xEFIxxDx (SEQ ID NO: 1), wherein D is aspartic acid, E is glutamic acid, F is phenylalanine, I is isoleucine and x is any other amino acid, wherein said peptide corresponds to the motif of SEQ ID NO: 1;

thus reducing the incidence of the ubiquitin-proteasome system binding to the cell surface receptor.

2. The method according to claim 1, wherein said cell surface receptor is a transport protein.

3. The method according to claim 2, wherein said transport protein is Glut4 insulin regulated glucose transporter.

4. The method according to claim 1, wherein said ubiquitin-proteasome system binding site is located in the intra-cellular part of said cell-surface receptor.

5. The method according to claim 1, wherein said peptide is capable of regulating the activity of a hormone.

6. The method according to claim 1, wherein said peptide is capable of controlling the availability and or signal transduction capability of said cell surface receptor.

7. The method according to claim 1, wherein said peptide interferes with said ubiquitin-proteasome system regulation of the cell surface receptors of said cell.

8. The method according to claim 1, wherein said peptide interferes with said ubiquitin-proteasome system regulation of the cell surface receptor of the cell by inhibiting ligand-induced receptor uptake.

9. The method according to claim 1, wherein said peptide interferes with said ubiquitin-proteasome system regulation of the cell surface receptor of the cell by inhibiting receptor degradation caused by endocytosis.

* * * * *

UNITED STATES PATENT AND TRADEMARK OFFICE
CERTIFICATE OF CORRECTION

PATENT NO. : 6,855,546 B1
APPLICATION NO. : 09/660302
DATED : February 15, 2005
INVENTOR(S) : Gerardus Jacobus Antonius Maria Strous et al.

It is certified that error appears in the above-identified patent and that said Letters Patent is hereby corrected as shown below:

On the title page:
In ITEM (75) Inventors,
2$^{nd}$ and 3$^{rd}$ lines, change "Petrus J. M. Van Kerkhof" to --Petrus J. M. van Kerkhof--

In the specification:

| | | |
|---|---|---|
| COLUMN 4, | LINE 25, | change "tibiquitin/proteasome" to --ubiquitin/proteasome-- |
| COLUMN 4, | LINE 55, | change "fructose-1,6-diphosphatase" to --fructose-1, 6-diphosphatase-- |
| COLUMN 6, | LINE 16, | change "1332 into alanine" to --I$^{332}$ into alanine-- |
| COLUMN 7, | LINE 6, | change "LAIHDSYKPEFHSDDSWVEFIELD IDEPDEKTEES-" to --LAIHDSYKPEFHSDDSWVEFIELDIDEPDEKTEES- -- |
| COLUMN 7, | LINE 8, | change "ETDFNANDIHEGTSE VAQPQRL" to --ETDFNANDIHEGTSEVAQPQRL-- |
| COLUMN 8, | LINE 36, | change "IGF-1 or 11," to --IGF-I or II,-- |
| COLUMN 9, | LINE 61, | change "were analyzed by SDS-PAGF;" to --were analyzed by SDS-PAGE;-- |
| COLUMN 12, | LINE 22, | change "PdrS (19)," to --Pdr5 (19),-- |

UNITED STATES PATENT AND TRADEMARK OFFICE
CERTIFICATE OF CORRECTION

PATENT NO. : 6,855,546 B1
APPLICATION NO. : 09/660302
DATED : February 15, 2005
INVENTOR(S) : Gerardus Jacobus Antonius Maria Strous et al.

It is certified that error appears in the above-identified patent and that said Letters Patent is hereby corrected as shown below:

In the specification (continued):
COLUMN 14, LINES 38-47, delete entire paragraph beginning with "Table 1, Abstract and Sequence Listing . . ." and ending with ". . . into the above-referenced patent application."

Signed and Sealed this

Thirtieth Day of September, 2008

JON W. DUDAS
*Director of the United States Patent and Trademark Office*

SEQUENCE LISTING

```
<160> NUMBER OF SEQ ID NOS: 51

<210> SEQ ID NO 1
<211> LENGTH: 8
<212> TYPE: PRT
<213> ORGANISM: Unknown
<220> FEATURE:
<221> NAME/KEY: BINDING
<222> LOCATION: (1)..(8)
<223> OTHER INFORMATION: synthetic peptide, Binding polypeptide motif
<220> FEATURE:
<221> NAME/KEY: UNSURE
<222> LOCATION: (1)..(1)
<223> OTHER INFORMATION: Xaa may be any amino acid
<220> FEATURE:
<221> NAME/KEY: UNSURE
<222> LOCATION: (5)..(5)
<223> OTHER INFORMATION: Xaa may be any amino acid
<220> FEATURE:
<221> NAME/KEY: UNSURE
<222> LOCATION: (6)..(6)
<223> OTHER INFORMATION: Xaa may be any amino acid
<220> FEATURE:
<221> NAME/KEY: UNSURE
<222> LOCATION: (8)..(8)
<223> OTHER INFORMATION: Xaa may be any amino acid

<400> SEQUENCE: 1

Xaa Glu Phe Ile Xaa Xaa Asp Xaa
1               5

<210> SEQ ID NO 2
<211> LENGTH: 12
<212> TYPE: PRT
<213> ORGANISM: Unknown
<220> FEATURE:
<223> OTHER INFORMATION: Unsure, Growth hormone receptor binding motif,
      Binds to hormone receptor and ubiquitin

<400> SEQUENCE: 2

Asp Asp Ser Trp Val Glu Phe Ile Glu Leu Asp Ile
```

-continued

```
1               5                   10
```

<210> SEQ ID NO 3
<211> LENGTH: 10
<212> TYPE: PRT
<213> ORGANISM: Unknown
<220> FEATURE:
<223> OTHER INFORMATION: Unsure, Growth hormone receptor motif, Binds to
      hormone receptor and ubiquitin

<400> SEQUENCE: 3

```
Asp Ser Trp Val Glu Phe Ile Glu Leu Asp
1               5                   10
```

<210> SEQ ID NO 4
<211> LENGTH: 129
<212> TYPE: PRT
<213> ORGANISM: Unknown
<220> FEATURE:
<223> OTHER INFORMATION: Unsure, Growth hormone receptor motif,
      Up-regulates GH activity

<400> SEQUENCE: 4

```
Ser Lys Gln Gln Arg Ile Lys Met Leu Ile Leu Pro Pro Val Pro Val
1               5                   10                  15

Pro Lys Ile Lys Gly Ile Asp Pro Asp Leu Leu Lys Glu Gly Lys Leu
            20                  25                  30

Glu Glu Val Asn Thr Ile Leu Ala Ile His Asp Ser Tyr Lys Pro Glu
        35                  40                  45

Phe His Ser Asp Asp Ser Trp Val Glu Phe Ile Glu Leu Asp Ile Asp
    50                  55                  60

Glu Pro Asp Glu Lys Thr Glu Glu Ser Asp Thr Asp Leu Leu Ser Ser
65                  70                  75                  80

Asp His Glu Lys Ser His Ser Asn Leu Gly Val Lys Asp Gly Asp Ser
                85                  90                  95

Gly Arg Thr Ser Cys Cys Glu Pro Asp Ile Leu Glu Thr Asp Phe Asn
            100                 105                 110

Ala Asn Asp Ile His Glu Gly Thr Ser Glu Val Ala Gln Pro Gln Arg
        115                 120                 125

Leu
```

<210> SEQ ID NO 5
<211> LENGTH: 38
<212> TYPE: PRT
<213> ORGANISM: Unknown
<220> FEATURE:
<223> OTHER INFORMATION: Unsure, Derived from protein receptor,
      Up-regulates GH activity

<400> SEQUENCE: 5

```
Lys Asp Gly Asp Ser Gly Arg Thr Ser Cys Cys Glu Pro Asp Ile Leu
1               5                   10                  15

Glu Thr Asp Phe Asn Ala Asn Phe Ile His Glu Gly Thr Ser Glu Val
            20                  25                  30

Ala Gln Pro Gln Arg Leu
            35
```

<210> SEQ ID NO 6
<211> LENGTH: 10
<212> TYPE: PRT
<213> ORGANISM: Unknown
<220> FEATURE:

```
<223> OTHER INFORMATION: Unsure, Glut4 Ins-regulated glucose transporter
      binding motif, Binds to ubiquitin/proteasome system binding site

<400> SEQUENCE: 6

Thr Glu Leu Glu Tyr Leu Gly Pro Asp Glu
1               5                   10

<210> SEQ ID NO 7
<211> LENGTH: 7
<212> TYPE: PRT
<213> ORGANISM: Unknown
<220> FEATURE:
<223> OTHER INFORMATION: Unsure, Binding poly-peptide motif, Binds to
      ubiquitin/proteasome system binding site

<400> SEQUENCE: 7

Cys Glu Glu Asp Phe Tyr Arg
1               5

<210> SEQ ID NO 8
<211> LENGTH: 10
<212> TYPE: PRT
<213> ORGANISM: Homo sapiens (human) or Lepus unknown species (rabbit)
<220> FEATURE:
<223> OTHER INFORMATION: GHR sequence

<400> SEQUENCE: 8

Ser Trp Val Glu Phe Ile Glu Leu Asp Ile
1               5                   10

<210> SEQ ID NO 9
<211> LENGTH: 10
<212> TYPE: PRT
<213> ORGANISM: Gallus gallus (chicken)
<220> FEATURE:
<223> OTHER INFORMATION: GHR

<400> SEQUENCE: 9

Leu Trp Val Glu Phe Ile Glu Leu Asp Ile
1               5                   10

<210> SEQ ID NO 10
<211> LENGTH: 10
<212> TYPE: PRT
<213> ORGANISM: Homo sapiens (human)
<220> FEATURE:
<223> OTHER INFORMATION: prolactin receptor

<400> SEQUENCE: 10

Leu Leu Val Glu Tyr Leu Glu Val Asp Asp
1               5                   10

<210> SEQ ID NO 11
<211> LENGTH: 10
<212> TYPE: PRT
<213> ORGANISM: Mus musculus (mouse), Lepus unknown species (rabbit), or
      Rattus unknown species (rat)
<220> FEATURE:
<223> OTHER INFORMATION: prolactin receptor

<400> SEQUENCE: 11

Leu Leu Val Glu Phe Leu Glu Asn Asp Asp
1               5                   10

<210> SEQ ID NO 12
<211> LENGTH: 10
<212> TYPE: PRT
```

```
<213> ORGANISM: Unknown
<220> FEATURE:
<223> OTHER INFORMATION: Unsure, vertebrate skeletal muscle

<400> SEQUENCE: 12

Asp Asn Val Asp Tyr Leu Thr Arg Asp Trp
1               5                   10

<210> SEQ ID NO 13
<211> LENGTH: 10
<212> TYPE: PRT
<213> ORGANISM: Unknown
<220> FEATURE:
<223> OTHER INFORMATION: Unsure, FGF Receptor Family

<400> SEQUENCE: 13

Gln Ala Ala Glu Tyr Leu Arg Ser Glu Thr
1               5                   10

<210> SEQ ID NO 14
<211> LENGTH: 10
<212> TYPE: PRT
<213> ORGANISM: Unknown
<220> FEATURE:
<223> OTHER INFORMATION: Unsure, Transmembrane receptor sex precursor

<400> SEQUENCE: 14

Ile Asp Ala Glu Tyr Ile Ser Ala Glu Arg
1               5                   10

<210> SEQ ID NO 15
<211> LENGTH: 10
<212> TYPE: PRT
<213> ORGANISM: Unknown
<220> FEATURE:
<223> OTHER INFORMATION: Unsure, IgE Receptor

<400> SEQUENCE: 15

Leu Lys Gly Glu Phe Ile Trp Val Asp Gly
1               5                   10

<210> SEQ ID NO 16
<211> LENGTH: 10
<212> TYPE: PRT
<213> ORGANISM: Unknown
<220> FEATURE:
<223> OTHER INFORMATION: Unsure, ANGIOTENSIN CONVERTING ENZYME

<400> SEQUENCE: 16

Tyr Gly Ser Glu Tyr Ile Asn Leu Asp Gly
1               5                   10

<210> SEQ ID NO 17
<211> LENGTH: 10
<212> TYPE: PRT
<213> ORGANISM: Unknown
<220> FEATURE:
<223> OTHER INFORMATION: Unsure, POTASSIUM CHANNEL IRK

<400> SEQUENCE: 17

Ser Glu Gly Glu Tyr Ile Pro Leu Asp Gln
1               5                   10

<210> SEQ ID NO 18
<211> LENGTH: 10
<212> TYPE: PRT
<213> ORGANISM: Unknown
```

```
<220> FEATURE:
<223> OTHER INFORMATION: Unsure, PDGF RECEPTOR ALPHA-CHAIN

<400> SEQUENCE: 18

Asp Gly His Glu Tyr Ile Tyr Val Asp Pro
1               5                   10

<210> SEQ ID NO 19
<211> LENGTH: 10
<212> TYPE: PRT
<213> ORGANISM: Unknown
<220> FEATURE:
<223> OTHER INFORMATION: Unsure, PDGF RECEPTOR BETA-CHAIN

<400> SEQUENCE: 19

Asp Gly His Glu Tyr Ile Tyr Val Asp Pro
1               5                   10

<210> SEQ ID NO 20
<211> LENGTH: 10
<212> TYPE: PRT
<213> ORGANISM: Homo sapiens (human), Lepus unknown species (rabbit), or
      Rattus unknown species (rat)
<220> FEATURE:
<223> OTHER INFORMATION: Ca++ -channel

<400> SEQUENCE: 20

Asp Asn Phe Glu Tyr Leu Thr Arg Asp Ser
1               5                   10

<210> SEQ ID NO 21
<211> LENGTH: 10
<212> TYPE: PRT
<213> ORGANISM: Unknown
<220> FEATURE:
<223> OTHER INFORMATION: Unsure, Cl- CHANNEL CLC7

<400> SEQUENCE: 21

Lys Ile Phe Glu Tyr Leu Arg Arg Asp Thr
1               5                   10

<210> SEQ ID NO 22
<211> LENGTH: 10
<212> TYPE: PRT
<213> ORGANISM: Homo sapiens (human)
<220> FEATURE:
<223> OTHER INFORMATION: TYROSINE-PROTEIN KINASE FRK

<400> SEQUENCE: 22

Ser Leu Gln Glu Tyr Leu Gln Asn Asp Thr
1               5                   10

<210> SEQ ID NO 23
<211> LENGTH: 10
<212> TYPE: PRT
<213> ORGANISM: Unknown
<220> FEATURE:
<223> OTHER INFORMATION: Unsure, GLUT4 INS-REGULATED GLUCOSE TRANSPORTER

<400> SEQUENCE: 23

Thr Glu Leu Glu Tyr Leu Gly Pro Asp Glu
1               5                   10

<210> SEQ ID NO 24
<211> LENGTH: 10
<212> TYPE: PRT
<213> ORGANISM: Rattus unknown species (Rat)
```

```
<220> FEATURE:
<223> OTHER INFORMATION: MHC-II(BETA)

<400> SEQUENCE: 24

Asn Gln Glu Glu Tyr Leu Arg Tyr Asp Ser
1               5                   10

<210> SEQ ID NO 25
<211> LENGTH: 10
<212> TYPE: PRT
<213> ORGANISM: Unkown
<220> FEATURE:
<223> OTHER INFORMATION: Unsure, ERB2 TKR (neu-oncogene)

<400> SEQUENCE: 25

Glu Asn Pro Glu Tyr Leu Gly Leu Asp Val
1               5                   10

<210> SEQ ID NO 26
<211> LENGTH: 10
<212> TYPE: PRT
<213> ORGANISM: Unkown
<220> FEATURE:
<223> OTHER INFORMATION: Unsure, ANION TRANSPORTER I

<400> SEQUENCE: 26

Arg Leu Lys Glu Tyr Leu Ala Gly Asp Val
1               5                   10

<210> SEQ ID NO 27
<211> LENGTH: 10
<212> TYPE: PRT
<213> ORGANISM: Unknown
<220> FEATURE:
<223> OTHER INFORMATION: Unsure, VASCULAR ENDOTHELIAL GROWTH FACTOR
      receptor 2

<400> SEQUENCE: 27

Leu Tyr Lys Asp Phe Leu Thr Leu Glu His
1               5                   10

<210> SEQ ID NO 28
<211> LENGTH: 10
<212> TYPE: PRT
<213> ORGANISM: Unknown
<220> FEATURE:
<223> OTHER INFORMATION: Unsure, VASCULAR ENDOTHELIAL GROWTH FACTOR
      receptor 3

<400> SEQUENCE: 28

Glu Gln Lys Glu Tyr Lys Ser Tyr Asp Ala
1               5                   10

<210> SEQ ID NO 29
<211> LENGTH: 10
<212> TYPE: PRT
<213> ORGANISM: Unknown
<220> FEATURE:
<223> OTHER INFORMATION: Unsure, G PROTEIN-ACT. INWARD RECTIFIER
      K+-CHANNEL-1

<400> SEQUENCE: 29

Pro Glu Gly Glu Phe Leu Pro Leu Asp Gln
1               5                   10

<210> SEQ ID NO 30
<211> LENGTH: 10
```

```
<212> TYPE: PRT
<213> ORGANISM: Homo sapiens (human)
<220> FEATURE:
<223> OTHER INFORMATION: PROTEIN-TYROSINE PHOSPHATASE ZETA

<400> SEQUENCE: 30

Ser Asp Ser Glu Phe Leu Leu Pro Asp Thr
1               5                   10

<210> SEQ ID NO 31
<211> LENGTH: 10
<212> TYPE: PRT
<213> ORGANISM: Unknown
<220> FEATURE:
<223> OTHER INFORMATION: Unsure, GLUTAMATE (NMDA) RECEPTOR SUBUNIT
      EPSILON 2

<400> SEQUENCE: 31

Ser Ala Leu Asp Phe Ile Arg Arg Glu Ser
1               5                   10

<210> SEQ ID NO 32
<211> LENGTH: 10
<212> TYPE: PRT
<213> ORGANISM: Unknown
<220> FEATURE:
<223> OTHER INFORMATION: Unsure, RHESUS BLOOD GROUP-ASSOCIATED
      GLYCOPROTEIN

<400> SEQUENCE: 32

Ala His Asn Glu Tyr Leu Val Ser Glu Ile
1               5                   10

<210> SEQ ID NO 33
<211> LENGTH: 10
<212> TYPE: PRT
<213> ORGANISM: Unknown
<220> FEATURE:
<223> OTHER INFORMATION: Unsure, DIHYDROPYRIDINE-SENSITIVE 1-TYPE,
      Ca++ Channel

<400> SEQUENCE: 33

Val Thr Leu Asp Phe Leu Asp Ala Glu Leu
1               5                   10

<210> SEQ ID NO 34
<211> LENGTH: 10
<212> TYPE: PRT
<213> ORGANISM: Unknown
<220> FEATURE:
<223> OTHER INFORMATION: Unsure, THROMBOPOIETIN RECEPTOR

<400> SEQUENCE: 34

Glu Ile Ser Asp Phe Leu Arg Tyr Glu Leu
1               5                   10

<210> SEQ ID NO 35
<211> LENGTH: 10
<212> TYPE: PRT
<213> ORGANISM: Unknown
<220> FEATURE:
<223> OTHER INFORMATION: Unsure, SEROTONIN RECEPTOR 1B (brain)

<400> SEQUENCE: 35

Ser Ala Lys Asp Tyr Ile Tyr Gln Asp Ser
1               5                   10
```

```
<210> SEQ ID NO 36
<211> LENGTH: 10
<212> TYPE: PRT
<213> ORGANISM: Unknown
<220> FEATURE:
<223> OTHER INFORMATION: Unsure, EPIDERMAL GROWTH FACTOR receptor

<400> SEQUENCE: 36

Tyr Gln Gln Asp Phe Phe Pro Lys Glu Ala
1               5                   10

<210> SEQ ID NO 37
<211> LENGTH: 10
<212> TYPE: PRT
<213> ORGANISM: Unknown
<220> FEATURE:
<223> OTHER INFORMATION: Unsure, SODIUM, CHLORIDE-DEPENDENT TRANSPORTER
      NTT4

<400> SEQUENCE: 37

Ser Lys Leu Gln Tyr Ile Leu Ala Gln Ile
1               5                   10

<210> SEQ ID NO 38
<211> LENGTH: 10
<212> TYPE: PRT
<213> ORGANISM: Unknown
<220> FEATURE:
<223> OTHER INFORMATION: Unsure, RHODOPSIN

<400> SEQUENCE: 38

Thr Pro Leu Asn Tyr Ile Leu Leu Asn Leu
1               5                   10

<210> SEQ ID NO 39
<211> LENGTH: 10
<212> TYPE: PRT
<213> ORGANISM: Unknown
<220> FEATURE:
<223> OTHER INFORMATION: Unsure, INTERLEUKIN-2 RECEPTOR BETA-CHAIN

<400> SEQUENCE: 39

Thr Ser Val Asp Leu Leu Asp Ile Asn Val
1               5                   10

<210> SEQ ID NO 40
<211> LENGTH: 10
<212> TYPE: PRT
<213> ORGANISM: Unknown
<220> FEATURE:
<223> OTHER INFORMATION: Unsure, cAMP-DEPENDENT PROTEIN KINASE C, ALPHA,
      BETA

<400> SEQUENCE: 40

Gly Thr Pro Asp Tyr Ile Ala Pro Glu Ile
1               5                   10

<210> SEQ ID NO 41
<211> LENGTH: 10
<212> TYPE: PRT
<213> ORGANISM: Unknown
<220> FEATURE:
<223> OTHER INFORMATION: Unsure, cAMP-DEPENDENT PROTEIN KINASE DELTA,
      EPSILON, GAMMA

<400> SEQUENCE: 41

Gly Thr Pro Glu Tyr Leu Ala Pro Glu Ile
1               5                   10
```

<210> SEQ ID NO 42
<211> LENGTH: 10
<212> TYPE: PRT
<213> ORGANISM: Unknown
<220> FEATURE:
<223> OTHER INFORMATION: Unsure, SERINE/THREONINE KINASE PCTAIRE 1,2

<400> SEQUENCE: 42

Leu Val Phe Glu Tyr Leu Asp Lys Asp Leu
1               5                   10

<210> SEQ ID NO 43
<211> LENGTH: 10
<212> TYPE: PRT
<213> ORGANISM: Unknown
<220> FEATURE:
<223> OTHER INFORMATION: Unsure, SERINE/THREONINE KINASE PCTAIRE 3

<400> SEQUENCE: 43

Leu Val Phe Glu Tyr Leu Asp Ser Asp Leu
1               5                   10

<210> SEQ ID NO 44
<211> LENGTH: 10
<212> TYPE: PRT
<213> ORGANISM: Unknown
<220> FEATURE:
<223> OTHER INFORMATION: Unsure, SMALL GTP-BINDING PROTEIN Rab-7

<400> SEQUENCE: 44

Ile Gly Ala Asp Phe Leu Thr Lys Glu Val
1               5                   10

<210> SEQ ID NO 45
<211> LENGTH: 10
<212> TYPE: PRT
<213> ORGANISM: Unknown
<220> FEATURE:
<223> OTHER INFORMATION: Unsure, SMALL GTP-BINDING PROTEIN Rab-9

<400> SEQUENCE: 45

Ile Gly Val Glu Phe Leu Asn Lys Asp Leu
1               5                   10

<210> SEQ ID NO 46
<211> LENGTH: 10
<212> TYPE: PRT
<213> ORGANISM: Unknown
<220> FEATURE:
<223> OTHER INFORMATION: Unsure, SYNAPTOTAGMIN IV

<400> SEQUENCE: 46

Ile Ser Val Glu Phe Leu Val Leu Asp Ser
1               5                   10

<210> SEQ ID NO 47
<211> LENGTH: 10
<212> TYPE: PRT
<213> ORGANISM: Unknown
<220> FEATURE:
<223> OTHER INFORMATION: Unsure, GLUTAMATE DECARBOXYLASE (GAD67)

<400> SEQUENCE: 47

Ser Asp Ile Asp Phe Leu Ile Glu Glu Ile
1               5                   10

<210> SEQ ID NO 48

-continued

```
<211> LENGTH: 10
<212> TYPE: PRT
<213> ORGANISM: Unknown
<220> FEATURE:
<223> OTHER INFORMATION: Unsure, FRUCTOSE 1,6 DIPHOSPHATASE (FBPase)

<400> SEQUENCE: 48

Ala Ile Gly Glu Phe Ile Leu Val Asp Lys
1               5                   10

<210> SEQ ID NO 49
<211> LENGTH: 10
<212> TYPE: PRT
<213> ORGANISM: Unknown
<220> FEATURE:
<223> OTHER INFORMATION: Unsure, CYSTIC FIBROSIS TRANSMEMBRANE
      CONDUCTANCE REGULATOR

<400> SEQUENCE: 49

Gln Lys Gln Glu Tyr Lys Thr Leu Glu Tyr
1               5                   10

<210> SEQ ID NO 50
<211> LENGTH: 5
<212> TYPE: PRT
<213> ORGANISM: Unknown
<220> FEATURE:
<223> OTHER INFORMATION: Unsure, EPITHELIAL Na+ CHANNEL
<220> FEATURE:
<221> NAME/KEY: UNSURE
<222> LOCATION: (4)..(4)
<223> OTHER INFORMATION: Xaa may be any amino acid

<400> SEQUENCE: 50

Pro Pro Pro Xaa Tyr
1               5

<210> SEQ ID NO 51
<211> LENGTH: 12
<212> TYPE: PRT
<213> ORGANISM: Unknown
<220> FEATURE:
<223> OTHER INFORMATION: Unsure

<400> SEQUENCE: 51

Ser Trp Val Glu Phe Ile Glu Leu Asp Ile Asp Asp
1               5                   10
```